United States Patent
Chou et al.

(10) Patent No.: US 7,601,831 B2
(45) Date of Patent: Oct. 13, 2009

(54) **METHODS, KITS AND ASSAY SYSTEM FOR DETECTING DRUG-RESISTANT *MYCOBACTERIUM TUBERCULOSIS***

(75) Inventors: George Chin-Sheng Chou, Tainan Hsien (TW); Chuang-Yi Huang, Tainan Hsien (TW)

(73) Assignee: AsiaGen Corporation, Tainan Nsien (TW)

( * ) Notice: Subject to any disclaimer, the term of this patent is extended or adjusted under 35 U.S.C. 154(b) by 48 days.

(21) Appl. No.: 11/896,807

(22) Filed: Sep. 6, 2007

(65) Prior Publication Data

US 2008/0145851 A1 Jun. 19, 2008

Related U.S. Application Data

(62) Division of application No. 10/833,097, filed on Apr. 28, 2004, now Pat. No. 7,445,895.

(51) Int. Cl.
*C07H 21/04* (2006.01)
*C07H 21/02* (2006.01)
*C12Q 1/68* (2006.01)

(52) U.S. Cl. .................. 536/24.32; 435/6; 435/243; 435/252.1; 435/253.1; 435/283.1; 436/501; 436/518; 436/519; 436/526; 536/23.1; 536/23.7; 536/24.3

(58) Field of Classification Search .................. 435/6, 435/243, 252.1, 253.1, 283.1; 436/501, 518, 436/519, 526; 536/23.1, 23.7, 24.3, 24.32
See application file for complete search history.

*Primary Examiner*—Rodney P. Swartz
(74) *Attorney, Agent, or Firm*—WPAT, P.C.; Anthony King; Kay Yang

(57) ABSTRACT

The present invention relates to methods, kits and assay system for detecting drug-resistant *Mycobacterium tuberculosis* of suspected patient. The system of the present invention largely reduces the whole process of drug-resistant *M. tuberculosis* detection in less than 5 hours.

2 Claims, 5 Drawing Sheets

```
┌─────────────────────────────────────────┐
│         Clinical samples accessible:    │
│    Sputum, serum, CSF, pleural effusion │
└─────────────────────────────────────────┘
                    ⇓
┌─────────────────────────────────────────┐
│  Bioactive primers mediated target amplification │
└─────────────────────────────────────────┘
                    ⇓
┌─────────────────────────────────────────┐
│        Proof-reading by drug-resistant  │
│        M. tuberculosis-specific probes  │
└─────────────────────────────────────────┘
                    ⇓
┌─────────────────────────────────────────┐
│           Detection by Luminometer      │
└─────────────────────────────────────────┘
```

FIG. 1

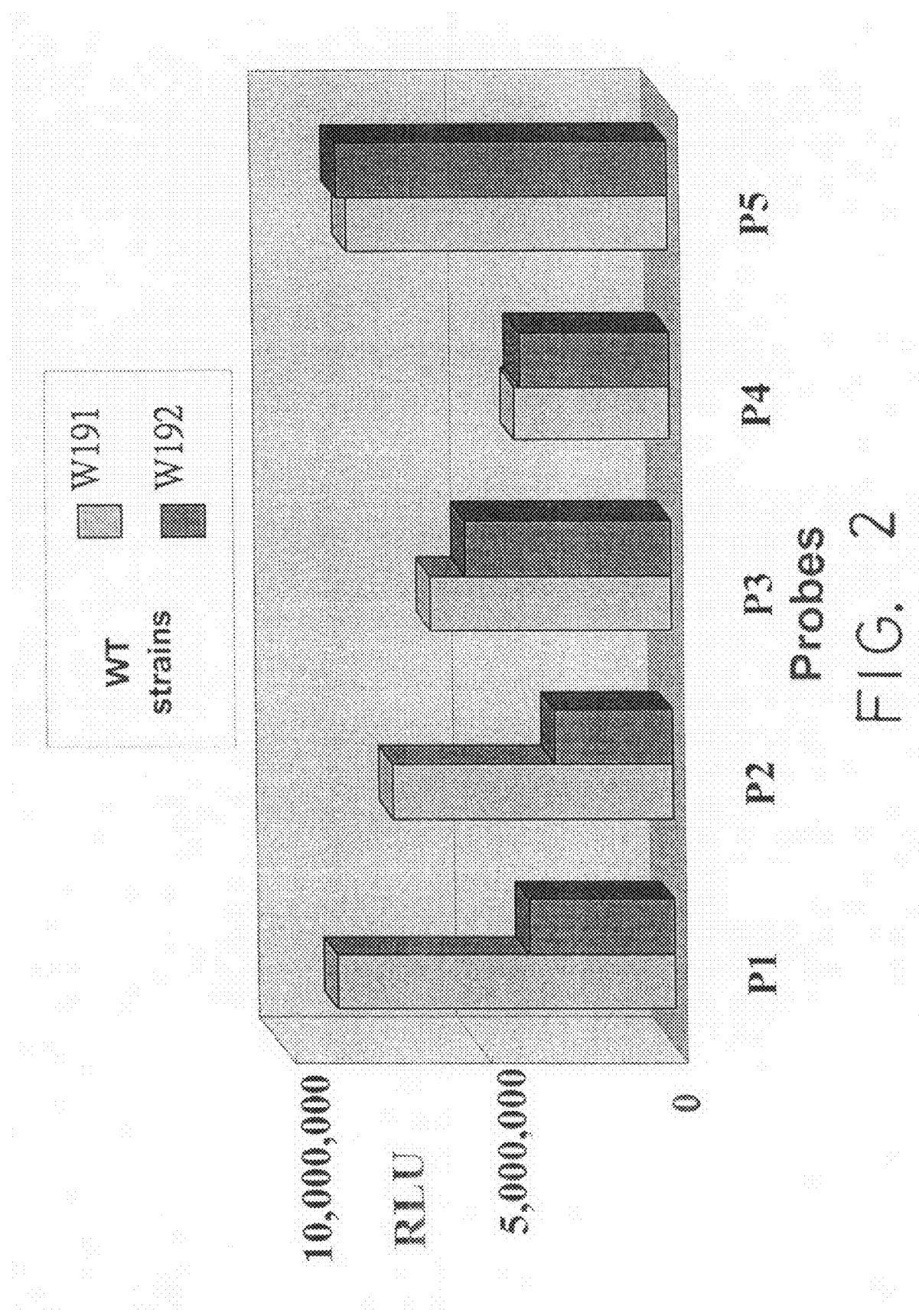

SEQUENCE LISTING

```
<160> NUMBER OF SEQ ID NOS: 40

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
cagccagctg agccaattca t                                             21

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
cagccagctg agccaattca tggac                                         25

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cagccagctg agccaattca tgga                                          24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
```

-continued

```
<400> SEQUENCE: 4
cagccagctg agccaattca tgg                                            23

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cagccagctg agccaattca tg                                             22

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cagccagctg agccaattc                                                 19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
cagccagctg agccaattca                                                20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
agccagctga gccaattcat gg                                             22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gccagctgag ccaattcatg ga                                             22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
```

```
gccagctgag ccaattccat g                                          21
```

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11

```
ttcatggacc agaacaaccc gct                                        23
```

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12

```
ttcatggacc agaacaaccc gc                                         22
```

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13

```
ttcatggacc agaacaaccc g                                          21
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14

```
ttcatggacc agaacaaccc                                            20
```

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15

```
ttcatggacc agaacaacc                                             19
```

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
attcatggac cagaacaacc cgc                     23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
aattcatgga ccagaacaac ccg                     23

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
caattcatgg accagaacaa ccc                     23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
ccaattcatg gaccagaaca acc                     23

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
caattcatgg accagaacaa c                       21

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
aattcatgga ccagaacaac ccgct                   25

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
cgactgtcgg cgctggggc                          19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
cgactgtcgg cgctggggcc                                          20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cgactgtcgg cgctggggcc c                                        21

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
cgactgtcgg cgctggggcc cg                                       22

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
cgactgtcgg cgctggggcc cgg                                      23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
cgactgtcgg cgctggggcc cggc                                     24

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
ccgactgtcg gcgctggggc                                          20

-continued

```
<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gccgactgtc ggcgctgggg c                                          21

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cgccgactgt cggcgctggg gc                                         22

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
gcgccgactg tcggcgctgg ggc                                        23

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
agcgccgact gtcggcgctg gggc                                       24

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
gactgtcggc gctggggcc                                             19

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
actgtcggcg ctggggccc                                             19
```

<210> SEQ ID NO 35
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
ctgtcggcgc tggggcccg                                              19

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
ccgactgtcg gcgctgggg                                              19

<210> SEQ ID NO 37
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
gccgactgtc ggcgctggg                                              19

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cgccgactgt cggcgctggg                                             20

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gcacgtcgcg gacctcc                                                17

<210> SEQ ID NO 40
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cgccgcgatc aaggag                                                 16

METHODS, KITS AND ASSAY SYSTEM FOR DETECTING DRUG-RESISTANT *MYCOBACTERIUM TUBERCULOSIS*

RELATED APPLICATIONS

This application is a Divisional Application of previous application U.S. Ser. No. 10/833,097, entitled "METHODS, KITS AND ASSAY SYSTEM FOR DETECTING DRUG-RESISTANT MYCOBACTERIUM TUBERCULOSIS", filed on Apr. 28, 2004, now U.S. Pat. No. 7,445,895.

FIELD OF THE INVENTION

The present invention relates to methods, kits and assay system for detecting drug-resistant *Mycobacterium tuberculosis* from samples of suspected patient.

BACKGROUND OF THE INVENTION

Tuberculosis (TB) is the leading infectious killer of youth and adults and the first most common infectious disease worldwide. One third of the world's population is currently infected and 20 million of those infected are active cases; TB will kill 30 million people this decade. More than 50 million people may already be infected with multidrug-resistant (MDR) strains of TB. Prior to MDR tuberculosis, the success rate of drug combination treatment was greater than 90%, even in AIDS patients. MDR tuberculosis, however, is not only highly infectious but also essentially incurable with a mortality of 50%.

Tuberculosis is caused by infection with *Mycobacterium tuberculosis*, a *bacillus* bacterium. It is spread by aerosol droplets and causes irreversible lung destruction. Recently, because of complications due to multidrug-resistant strains, the number and combination of antibiotics administered must be individually tailored depending on the strain the patient is harboring. In general, manifest disease with an MDR strain of *Mycobacterium tuberculosis*—a strain resistant to both isoniazid and rifampin, and possibly to additional drugs—has a poor clinical outcome since efficient therapeutic strategies are still lacking.

Initially, antimicrobial susceptibility testing of *Mycobacterium tuberculosis* is carried out with a primary set of drugs, consisting of the front-line drugs isoniazid, rifampin, ethambutol, pyrazinamide, and, optionally, streptomycin. If resistance to one or several of these drugs is detected, it is common practice to test an extended spectrum of antimicrobial compounds.

For quite some time three different growth-based laboratory methods have been accepted for determining antimicrobial susceptibility of *Mycobacterium tuberculosis*: (1) the resistance ratio method, (2) the absolute concentration method, and (3) the proportion method. Most laboratories in the Western hemisphere utilize a modified proportion method on solid medium. For most of the major antituberculous agents, this technique defines resistance of *Mycobacterium tuberculosis* as a percentage of resistant organisms larger than 1 percent in a given population of bacilli.

Because antimicrobial susceptibility testing on solid media requires visible growth of the organisms (which requires three weeks of incubation), testing is preferentially done in liquid media today.

In the last decade antimicrobial susceptibility testing has become a dynamic field spawning many new technologies. They all comply with the standard set by the Centers for Disease Control and Prevention that susceptibility testing results for *Mycobacterium tuberculosis* have to be available within 28 days of the time the specimen arrives in the laboratory (Bird B R. et al, J Clin Microbiol 996;34:554-559.).

An increasing number of approaches assess drug susceptibility by identifying alternative markers of drug-resistant metabolic activities. Among those are colorimetry, flow cytometry (Norden, M A. et al, J Clin Microbiol 1995; 33:1231-1237), bioluminescence assay of mycobacterial adenosine triphosphate (Nilsson, L E et al, Antimicrob Agents Chemother 1988; 32:1208-1212.), and quantitation of mycobacterial antigens (Drowart, A. et al., Int J Tuberc Lung Dis 1997; 1:284-288.). Mycobacteriophage-based methods, for example, with luciferase reporter phages or PhaB phages, appear to be promising as well (Jacobs, W Jr et al., Science 1993; 260:819-822). However, the complexities of these technologies and high cost have largely hampered their wider application in the clinical mycobacteriology laboratory.

Molecular biology as a tool to detect resistant TB. *Mycobacterium tuberculosis* resistance to drugs always results from mutations. These mutations are either deleterious for the bacterial cell or, conversely, alter the structure of a protein targeted by a drug without compromising the protein's function for the microorganism. In *Mycobacterium tuberculosis* these mutations appear to be confined to chromosomal DNA and do not involve mobile genetic elements (such as plasmids).

In particular, DNA sequencing, but also other techniques such as gel electrophoresis (single-stranded conformation polymorphism [SSCP]-PCR, dideoxy fingerprinting) and hybridization on solid phase (line probe assay, DNA chip technology) or on liquid phase (heteroduplex analysis, mismatch cleaving assay, molecular beacon) can identify those subtle mutations.

Resistance to rifampin, the most important component of current treatment regimens, is associated with a short core region consisting of 27 amino acids in the rpoB gene, which codes for the β subunit of RNA polymerase (Telenti, A. et al, Lancet 1993; 341:647-650). The ethambutol resistance-determining region (ERDR) has been proposed as a mutational hot spot in the embB gene, whereas the situation with pyrazinamide resistance is less clear. Resistance to isoniazid appears to be the complex result of single or multiple mutations in the katG, inhA, oxyR-ahpC, and/or kasA gene(s) (Heym, B. et al, Lancet 1994; 344:293-298.). Similarly, mutations in the rpsL and/or rrs gene(s) correlate with resistance in approximately 80 percent of streptomycin-resistant strains (Böttger, E C. Trends Microbiol 1994; 2:416-421).

In light of the worsening global TB epidemic and the extreme vulnerability of HIV-infected individuals to TB, rapid and reliable antimicrobial susceptibility testing in the laboratory is paramount for proper management of patients, particularly those with MDR TB.

Given the above, current available assay cannot quickly and completely detect drug-resistant *Mycobacterium tuberculosis*. It requires a quick assay with high specificity and sensitivity to detect drug-resistant *Mycobacterium tuberculosis* from available samples, especially from sputum of suspected patients.

SUMMARY OF THE INVENTION

The present invention relates to methods, kits and assay system for detecting drug-resistant *Mycobacterium tuberculosis* from the samples of suspected patient.

BRIEF DESCRIPTION OF THE DRAWINGS

FIG. 1 shows the outline of the detection method of the invention.

FIG. 2 shows the result of identifying drug-sensitive *Mycobacterium tuberculosis* using probe P1, P2, P3, P4 and P5.

DETAILED DESCRIPTION OF THE PREFERRED EMBODIMENTS

Figure 3:
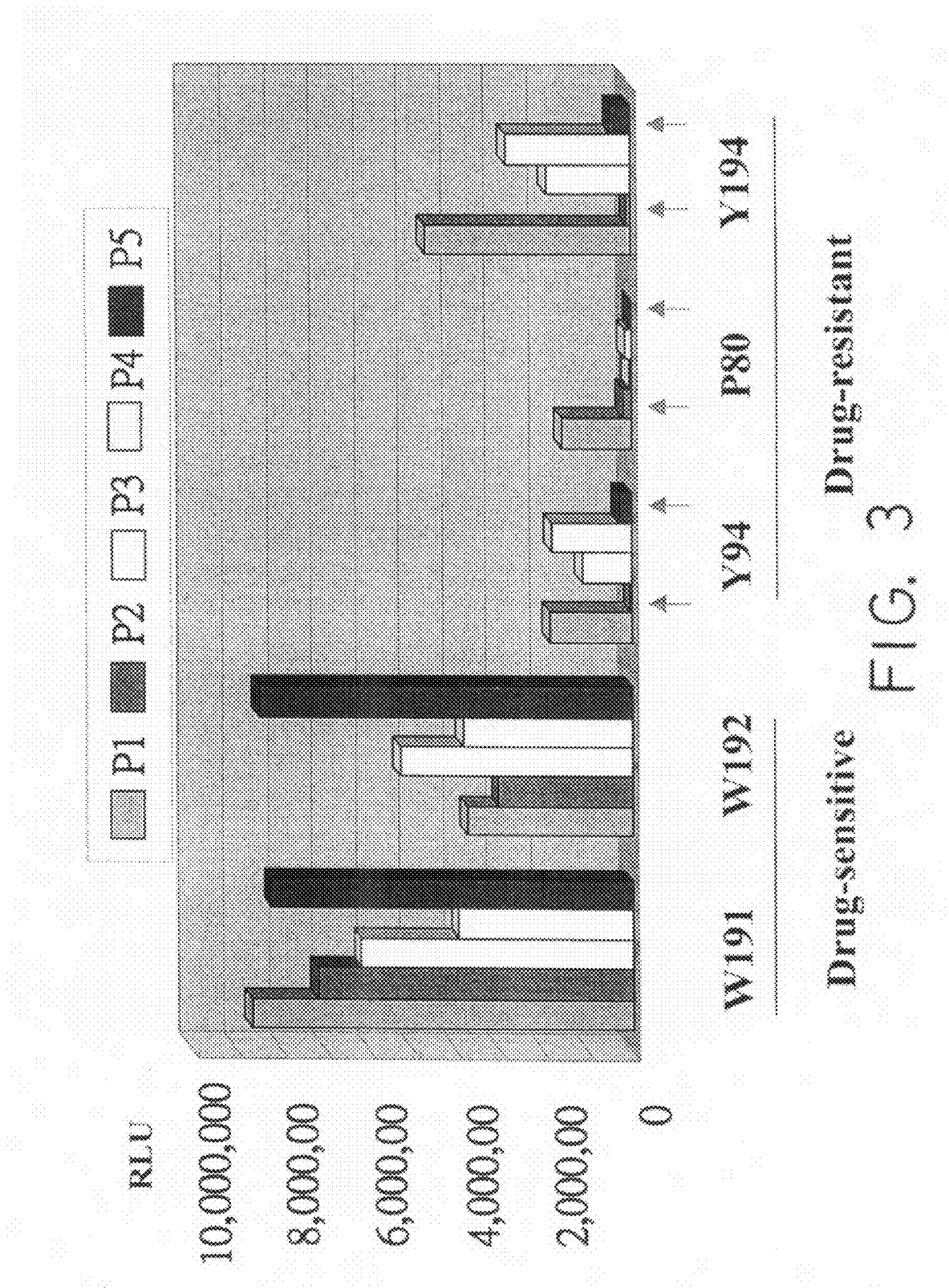
FIG. 3 shows the differentiation of drug-sensitive *Mycobacterium tuberculosis* strains W191 and W 192 from drug-resistant *Mycobacterium tuberculosis* Y94, P80 and Y194 using probe P1, P2, P3, P4 and P5.

The present invention provides a method for detecting drug-resistant *Mycobacterium tuberculosis* DNA comprising:
(a) hybridizing the drug-resistant *Mycobacterium tuberculosis* cDNA with drug-resistant *Mycobacterium tuberculosis*-specific probes in hybridization tubes;
(b) adding blocking solution into the tubes;
(c) adding avidin enzyme complex or streptavidin enzyme complex into the tubes;
(d) performing washing reaction to remove interfering material;
(e) adding substrate of enzyme; and
(f) detecting the luminescent or color change adding substrate of enzyme.

The probe may be linked to a magnetic bead. In the method of the invention, it further comprises transferring hybridization tubes to magnetic wells for washing between steps (a) and (b).

In general, any biological sample such as CSF, serum, blood, sputum, pleural effusion and throat swab and stools can be used in the clinical tests. The preferred samples for drug-resistant *Mycobacterium tuberculosis* are from CSF, serum, blood, sputum, pleural effusion, throat swab. The method of the invention is shown in FIG. 1.

Polymerase Chain Reaction (PCR) PCR is described in Saiki et al. (1985), Science, 230 1350. PCR consists of repeated cycles of DNA polymerase generated primer extension reactions. The target DNA is heat denatured and two oligonucleotides, which bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target DNA can be amplified a million fold or more in about two to four hours. PCR is a molecular biology tool that must be used in conjunction with a detection technique to determine the results of amplification. In the present invention, biotinylated primer pairs are used in the PCR amplification.

As used herein, a "probe" is a substance, e.g., a molecule, which can be specifically recognized by a particular target. Generally, probes will be linked to solid support to facilitate the separation of DNA. In the invention, the probes linked to magnetic beads (MagProbe) are preferred. At least one of the sequence of the probe in MagProbe can be selected from the group consisting of:

P1:
1. 5'-CAGCCAGCTGAGCCAATTCAT-3'        (SEQ ID NO:1)
2. 5'-CAGCCAGCTGAGCCAATTCATGGAC-3'   (SEQ ID NO:2)
3. 5'-CAGCCAGCTGAGCCAATTCATGGA-3'    (SEQ ID NO:3)
4. 5'-CAGCCAGCTGAGCCAATTCATGG-3'     (SEQ ID NO:4)
5. 5'-CAGCCAGCTGAGCCAATTCATG-3'      (SEQ ID NO:5)
6. 5'-CAGCCAGCTGAGCCAATTC-3'         (SEQ ID NO:6)
7. 5'-CAGCCAGCTGAGCCAATTCA-3'        (SEQ ID NO:7)
8. 5'-AGCCAGCTGAGCCAATTCATGG-3'      (SEQ ID NO:8)
9. 5'-GCCAGCTGAGCCAATTCATGGA-3'      (SEQ ID NO:9)
10. 5'-GCCAGCTGAGCCAATTCCATG-3'      (SEQ ID NO:10)

P2:
1. 5'-TTCATGGACCAGAACAACCCGCT -3'    (SEQ ID NO:11)
2. 5'-TTCATGGACCAGAACAACCCGC -3'     (SEQ ID NO:12)
3. 5'-TTCATGGACCAGAACAACCCG -3'      (SEQ ID NO:13)
4. 5'-TTCATGGACCAGAACAACCC -3'       (SEQ ID NO:14)
5. 5'-TTCATGGACCAGAACAACC -3'        (SEQ ID NO:15)
6. 5'-ATTCATGGACCAGAACAACCCGC -3'    (SEQ ID NO:16)
7. 5'-AATTCATGGACCAGAACAACCCG -3'    (SEQ ID NO:17)
8. 5'-CAATTCATGGACCAGAACAACCC -3'    (SEQ ID NO:18)
9. 5'-CCAATTCATGGACCAGAACAACC -3'    (SEQ ID NO:19)
10. 5'-CAATTCATGGACCAGAACAAC -3'     (SEQ ID NO:20)
11. 5'-AATTCATGGACCAGAACAACCCGCT -3' (SEQ ID NO:21)

P5:
1. 5'-CGACTGTCGGCGCTGGGGC-3'         (SEQ ID NO:22)
2. 5'-CGACTGTCGGCGCTGGGGCC-3'        (SEQ ID NO:23)
3. 5'-CGACTGTCGGCGCTGGGGCCC-3'       (SEQ ID NO:24)
4. 5'-CGACTGTCGGCGCTGGGGCCCG-3'      (SEQ ID NO:25)
5. 5'-CGACTGTCGGCGCTGGGGCCCGG-3'     (SEQ ID NO:26)
6. 5'-CGACTGTCGGCGCTGGGGCCCGGC-3'    (SEQ ID NO:27)
7. 5'-CCGACTGTCGGCGCTGGGGC-3'        (SEQ ID NO:28)
8. 5'-GCCGACTGTCGGCGCTGGGGC-3'       (SEQ ID NO:29)
9. 5'-CGCCGACTGTCGGCGCTGGGGC-3'      (SEQ ID NO:30)
10. 5'-GCGCCGACTGTCGGCGCTGGGGC-3'    (SEQ ID NO:31)
11. 5'-AGCGCCGACTGTCGGCGCTGGGGC-3'   (SEQ ID NO:32)

-continued

| | | |
|---|---|---|
| 12. 5'-GACTGTCGGCGCTGGGGCC-3' | (SEQ ID NO:33) |
| 13. 5'-ACTGTCGGCGCTGGGGCCC-3' | (SEQ ID NO:34) |
| 14. 5'-CTGTCGGCGCTGGGGCCCG-3' | (SEQ ID NO:35) |
| 15. 5'-CCGACTGTCGGCGCTGGGG-3' | (SEQ ID NO:36) |
| 16. 5'-GCCGACTGTCGGCGCTGGG-3' | (SEQ ID NO:37) |
| 17. 5'-CGCCGACTGTCGGCGCTGGG-3' | (SEQ ID NO:38) |

The oligomer probes described by SEQ ID NOs. 1 to 38 were constructed to hybridize with a specific DNA sequence of drug-resistant *Mycobacterium tuberculosis*.

Detectable labels suitable for use in the present invention include any composition detectable by spectroscopic, photochemical, biochemical, immunochemical, electrical, optical or chemical means. Useful labels in the present invention include biotin for combining with labeled streptavidin conjugate, magnetic beads (e.g., Dynabeads™), fluorescent dyes (e.g., fluorescein, texas red, rhodamine, green fluorescent protein, and the like), radiolabels (e.g., .H3, I125, .S35, .C14, or P32), enzymes (e.g., horse radish peroxidase, alkaline phosphatase and others commonly used in an ELISA), and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The preferred embodiment of the label is biotin. When biotin is employed, it is detected by avidin, streptavidin or the like, which is conjugated to a detectable marker, such as an enzyme (e.g., horseradish peroxidase). Enzyme conjugates are commercially available from, for example, Vector Laboratories (Burlingame, Calif.). Steptavidin binds with high affinity to biotin, unbound streptavidin is washed away, and the presence of horseradish peroxidase enzyme is then detected using a luminescence-emission substrate in the presence of peroxide and appropriate buffers. The product may be detected using a Berthold Luminometer (Pforzheim, Germany).

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays," Elsevier, N.Y., (1993). Stringency can be controlled by changing temperature, salt concentration, the presence of organic compounds, such as formamide or DMSO, or all of these. The effects of changing these parameters are well known in the art. Changes in the temperature are generally a preferred means of controlling stringency for convenience, ease of control, and reversibility.

The present invention also provides a diagnostic kit for detecting drug-resistant *Mycobacterium tuberculosis* cDNA comprising:

(a) a probe linked to a magnetic bead;
(b) bioactive primers;
(c) avidin enzyme complex or streptavidin enzyme complex; and
(d) enzyme substrate.

wherein the probe is selected from the group consisting of

```
5'-CAGCCAGCTGAGCCAATTCAT-3',          (SEQ ID NO:1)

5'-CAGCCAGCTGAGCCAATTCATGGAC-3',      (SEQ ID NO:2)

5'-CAGCCAGCTGAGCCAATTCATGGA-3',       (SEQ ID NO:3)

5'-CAGCCAGCTGAGCCAATTCATGG-3',        (SEQ ID NO:4)

5'-CAGCCAGCTGAGCCAATTCATG-3',         (SEQ ID NO:5)

5'-CAGCCAGCTGAGCCAATTC-3',            (SEQ ID NO:6)

5'-CAGCCAGCTGAGCCAATTCA-3',           (SEQ ID NO:7)

5'-AGCCAGCTGAGCCAATTCATGG-3',         (SEQ ID NO:8)

5'-GCCAGCTGAGCCAATTCATGGA-3',         (SEQ ID NO:9)

5'-GCCAGCTGAGCCAATTCCATG-3',          (SEQ ID NO:10)

5'-TTCATGGACCAGAACAACCCGCT -3',       (SEQ ID NO:11)

5'-TTCATGGACCAGAACAACCCGC -3',        (SEQ ID NO:12)

5'-TTCATGGACCAGAACAACCCG -3',         (SEQ ID NO:13)

5'-TTCATGGACCAGAACAACCC -3',          (SEQ ID NO:14)

5'-TTCATGGACCAGAACAACC -3',           (SEQ ID NO:15)

5'-ATTCATGGACCAGAACAACCCGC -3',       (SEQ ID NO:16)

5'-AATTCATGGACCAGAACAACCCG -3',       (SEQ ID NO:17)

5'-CAATTCATGGACCAGAACAACCC -3',       (SEQ ID NO:18)

5'-CCAATTCATGGACCAGAACAACC -3',       (SEQ ID NO:19)

5'-CAATTCATGGACCAGAACAAC -3',         (SEQ ID NO:20)

5'-AATTCATGGACCAGAACAACCCGCT -3',     (SEQ ID NO:21)

5'-CGACTGTCGGCGCTGGGGC-3',            (SEQ ID NO:22)

5'-CGACTGTCGGCGCTGGGGCC-3',           (SEQ ID NO:23)

5'-CGACTGTCGGCGCTGGGGCCC-3',          (SEQ ID NO:24)

5'-CGACTGTCGGCGCTGGGGCCCG-3',         (SEQ ID NO:25)

5'-CGACTGTCGGCGCTGGGGCCCGG-3',        (SEQ ID NO:26)

5'-CGACTGTCGGCGCTGGGGCCCGGC-3',       (SEQ ID NO:27)

5'-CCGACTGTCGGCGCTGGGGC-3',           (SEQ ID NO:28)

5'-GCCGACTGTCGGCGCTGGGGC-3',          (SEQ ID NO:29)

5'-CGCCGACTGTCGGCGCTGGGGC-3',         (SEQ ID NO:30)

5'-GCGCCGACTGTCGGCGCTGGGGC-3',        (SEQ ID NO:31)

5'-AGCGCCGACTGTCGGCGCTGGGGC-3',       (SEQ ID NO:32)

5'-GACTGTCGGCGCTGGGGCC-3',            (SEQ ID NO:33)

5'-ACTGTCGGCGCTGGGGCCC-3',            (SEQ ID NO:34)

5'-CTGTCGGCGCTGGGGCCCG-3',            (SEQ ID NO:35)

5'-CCGACTGTCGGCGCTGGGG-3',            (SEQ ID NO:36)
```

```
5'-GCCGACTGTCGGCGCTGGG-3',          (SEQ ID NO:37)
5'-CGCCGACTGTCGGCGCTGGG-3'.         (SEQ ID NO:38)
```

In the kit, the bioactive primers are made by reacting DNA labeling reagent with the primers. The DNA labeling reagent is one reagent labeling DNA. The preferred reagent is not limited but the compound having the formula:

Fu-BE-D wherein Fu represents a furocoumarin derivative selected from the group consisting of angelicin derivatives and psoralen derivatives; wherein BE represents none or a binding enhancer selected from the group consisting of $C_{4-12}$ alkyl, alkyenyl, polyalkylamine and polyethylene glycol; and wherein D represents a detectable group selected from the group consisting of: biotin, fluorescence, acridinium ester and acridinium-9-carboxamide. The most preferred DNA labeling reagent is 9-(4"-(Aminomethyl)-4',5"-Dimethyl-angelicin) acridinium carboxamide.

An assay system for detecting microorganisms, the system comprising:
(i) diagnostic kit for detecting drug-resistant *Mycobacterium tuberculosis* cDNA comprising:
   (a) a probe linked to magnetic bead;
   (b) bioactive primers;
   (c) avidin enzyme complex or streptavidin enzyme complex; and
   (d) enzyme substrate wherein the probe is selected from the group consisting of

```
5'-CAGCCAGCTGAGCCAATTCAT-3',        (SEQ ID NO:1)
5'-CAGCCAGCTGAGCCAATTCATGGAC-3',    (SEQ ID NO:2)
5'-CAGCCAGCTGAGCCAATTCATGGA-3',     (SEQ ID NO:3)
5'-CAGCCAGCTGAGCCAATTCATGG-3',      (SEQ ID NO:4)
5'-CAGCCAGCTGAGCCAATTCATG-3',       (SEQ ID NO:5)
5'-CAGCCAGCTGAGCCAATTC-3',          (SEQ ID NO:6)
5'-CAGCCAGCTGAGCCAATTCA-3',         (SEQ ID NO:7)
5'-AGCCAGCTGAGCCAATTCATGG-3',       (SEQ ID NO:8)
5'-GCCAGCTGAGCCAATTCATGGA-3',       (SEQ ID NO:9)
5'-GCCAGCTGAGCCAATTCCATG-3',        (SEQ ID NO:10)
5'-TTCATGGACCAGAACAACCCGCT -3',     (SEQ ID NO:11)
5'-TTCATGGACCAGAACAACCCGC -3',      (SEQ ID NO:12)
5'-TTCATGGACCAGAACAACCCG -3',       (SEQ ID NO:13)
5'-TTCATGGACCAGAACAACCC -3',        (SEQ ID NO:14)
5'-TTCATGGACCAGAACAACC -3',         (SEQ ID NO:15)
5'-ATTCATGGACCAGAACAACCCGC -3',     (SEQ ID NO:16)
5'-AATTCATGGACCAGAACAACCCG -3',     (SEQ ID NO:17)
5'-CAATTCATGGACCAGAACAACCC -3',     (SEQ ID NO:18)
5'-CCAATTCATGGACCAGAACAACC -3',     (SEQ ID NO:19)
5'-CAATTCATGGACCAGAACAAC -3',       (SEQ ID NO:20)
5'-AATTCATGGACCAGAACAACCCGCT -3',   (SEQ ID NO:21)
5'-CGACTGTCGGCGCTGGGGC-3',          (SEQ ID NO:22)
5'-CGACTGTCGGCGCTGGGGCC-3',         (SEQ ID NO:23)
5'-CGACTGTCGGCGCTGGGGCCC-3',        (SEQ ID NO:24)
5'-CGACTGTCGGCGCTGGGGCCCG-3',       (SEQ ID NO:25)
5'-CGACTGTCGGCGCTGGGGCCCGG-3',      (SEQ ID NO:26)
5'-CGACTGTCGGCGCTGGGGCCCGGC-3',     (SEQ ID NO:27)
5'-CCGACTGTCGGCGCTGGGGC-3',         (SEQ ID NO:28)
5'-GCCGACTGTCGGCGCTGGGGC-3',        (SEQ ID NO:29)
5'-CGCCGACTGTCGGCGCTGGGGC-3',       (SEQ ID NO:30)
5'-GCGCCGACTGTCGGCGCTGGGC-3',       (SEQ ID NO:31)
5'-AGCGCCGACTGTCGGCGCTGGGGC-3',     (SEQ ID NO:32)
5'-GACTGTCGGCGCTGGGGCC-3',          (SEQ ID NO:33)
5'-ACTGTCGGCGCTGGGGCCC-3',          (SEQ ID NO:34)
5'-CTGTCGGCGCTGGGGCCCG-3',          (SEQ ID NO:35)
5'-CCGACTGTCGGCGCTGGGG-3',          (SEQ ID NO:36)
5'-GCCGACTGTCGGCGCTGGG-3',          (SEQ ID NO:37)
5'-CGCCGACTGTCGGCGCTGGG-3'.         (SEQ ID NO:38)
```

(ii) an apparatus for performing the dissociation of nucleic acid double strands, hybridization, washing, the separation of magnetic beads and thermal control in the same apparatus, comprising:
   (a) the means for fitting reaction containers;
   (b) the means for controlling the temperature of the containers; and
   (c) the means for controlling the magnetic force of the containers, wherein the means for controlling the temperature of the containers are connected to the means for fitting reaction containers, and the means for controlling the magnetic force of the containers are connected to the means for fitting reaction containers;
(iii) a magnetic rack to bind the magnetic bead on the wall of the containers; and
(iv) a detector.

In the assay system of the invention, the kit further comprises hybridization buffer, washing buffer and blocking buffer. These buffers are easily purchased from commercial suppliers such as those of Pierce, Biolab, Qiagen etc. In general, the assay system of the invention can reduce the whole process of drug-resistant *Mycobacterium tuberculosis* detection to less than 5 hours.

Definitions and Terms

Unless defined otherwise, all scientific and technical terms used herein have the same meaning as commonly understood by those skilled in the relevant art. General definitions are provided, for example, in Dictionary of Microbiology and Molecular Biology, 2nd ed. (Singleton et al., 1994, John Wiley & Sons, New York, N.Y.) or The Harper Collins Dictionary of Biology (Hale & Marham, 1991, Harper Perennial, New York, N.Y.). Unless mentioned otherwise, the techniques employed or contemplated herein are well known standard methods in the art.

Units, prefixes, and symbols are denoted in their System International de Unites (SI) accepted form. Numeric ranges are inclusive of the numbers defining the range. Unless otherwise indicated, nucleic acids are written left to right in 5' to 3' orientation. The headings provided herein are not limitations of the various aspects or embodiments of the invention, which can be had by reference to the specification as a whole. Accordingly, the terms defined immediately below are more fully defined by reference to the specification in its entirety.

By "biological sample" is meant any tissue or material derived from a living or dead human which may contain M Mycobacterium tuberculosis nucleic acid. Samples include, for example, CSF, serum, blood, sputum, pleural effusion, throat swab and stools, respiratory tissue or exudates, plasma, cervical swab samples, biopsy tissue, gastrointestinal tissue, urine, feces, semen or other body fluids, tissues or materials. Samples also include bacterial cultures (from liquid or solid media) and environmental samples. A biological sample may be treated to physically disrupt tissue or cell structure, thus releasing intracellular components into a solution which may contain enzymes, buffers, salts, detergents and the like which are used to prepare the sample for analysis.

By "nucleic acid" is meant a multimeric compound comprising nucleosides or nucleoside analogs which have nitrogenous heterocyclic bases, or base analogs, where the nucleosides are covalently linked via a backbone structure to form a polynucleotide. Conventional RNA, DNA, and analogs of RNA and DNA are included in this term. A nucleic acid backbone may comprise a variety of known linkages, including one or more of sugar-phosphodiester linkages, peptide-nucleic acid bonds ("peptide nucleic acids"; PCT No. WO 95/32305 (Hydig-Hielsen et al.)), phosphorothioate linkages, methylphosphonate linkages or combinations of known linkages. Sugar moieties of the nucleic acid may be ribose or deoxyribose, or similar compounds having known substitutions, e.g., 2' methoxy and/or 2' halide substitutions. Nitrogenous bases may be conventional bases (A, G, C, T, U), known base analogs (e.g., inosine; see The Biochemistry of the Nucleic Acids 5-36, Adams et al., ed., 11.sup.th ed., 1992), or known derivatives of purine or pyrimidine bases (PCT No. WO 93/13121 (Cook)) and a "basic" residues in which the backbone includes no nitrogenous base for one or more residues (U.S. Pat. No. 5,585,481 (Arnold et al.)). A nucleic acid may comprise only conventional sugars, bases and linkages, as found in RNA and DNA, or may include both conventional components and substitutions (e.g., conventional bases linked via a methoxy backbone, or a nucleic acid including conventional bases and one or more analogs).

By "probe" is meant a nucleic acid oligomer that hybridizes specifically to a target sequence in a nucleic acid or its complement, preferably in an amplified nucleic acid, under conditions that promote hybridization, thereby allowing detection of the target or amplified nucleic acid. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). A probe's "target" generally refers to a sequence in (i.e., a subset of) a larger nucleic acid sequence that hybridizes specifically to at least a portion of the probe sequence by standard hydrogen bonding (base pairing). Sequences that are "sufficiently complementary" allow stable hybridization of a probe oligomer to a target sequence, even if the two sequences are not completely complementary. A probe may be labeled or unlabeled, depending on the detection method used, which methods are well known in the art.

By "separating" or "purifying" is meant that one or more components of the biological sample are removed from other sample components. Sample components generally are an aqueous solution that includes nucleic acids and other materials (e.g., proteins, carbohydrates, lipids and/or nucleic acids). A separating or purifying step removes at least about 70%, preferably at least about 90%, and more preferably at least about 95% of the other sample components.

References here to Mycobacterium tuberculosis refer to Mycobacterium tuberculosis. The sequence of the entire genome of Mycobacterium tuberculosis is set forth in TubercuList.

EXAMPLES

The examples below are non-limiting and are merely representative of various aspects and features of the present invention.

Example 1

Material and Methods

Major Kit I:
1. Lysis Buffer I (5 ml)
2. Lysis Buffer II (4 ml)
3. Hybridization Buffer (5 ml)
4. Wash Buffer (60 ml)
5. Lysis tubes (1.8 ml, 25 tubes)
6. Hybridization tubes (12×75 mm, 50 tubes)
7. Extension buffer (3 ml, stored in −20° C. after arriving)

Major Kit-II:(50 reactions/kit, store in 4° C.)
1. MagProbe (450 µl, stored in 4° C. after arriving)
Detection kit-I:(250 reactions/kit, store in 4° C.)
1. Blocking buffer (0.5%, 60 ml, stored in 4° C.)
2. Horseradish Peroxidase (HRP) Substrate A (7.5 ml, stored in 4° C.)
3. HRP Substrate B (7.5 ml, stored in 4° C.)

Detection kit-II: (250 reactions/kit, store in −20° C.)
1. Bioactive catalyst (Straptavidin-HRP; BC; 1 mg/ml, 15 µl, stored in −20° C.)
2. Other material and equipments:
1. Magnetic Rack
2. NALC (N-acetyl-L-cysteine)
3. 4% NaOH solution
4. 2.94% sodium citrate solution
5. PBS, pH7.0
6. 0.1% PBST (PBS with 0.1% tween-20)
7. 0.5% PBST (PBS with 0.5% tween-20)
8. Magnetic Dry Bath
9. Berthol Luminometer with PC connection Procedures:

I. Decontamination of Clinical Samples (Performed in P3 Level Laboratory)
1. Collect and keep clinical samples in 4° C. refrigerator.
2. Dissolve 1 g of NALC into 100 ml of sterile 4% NaOH and 100 ml of 2.94% sodium citrate solution (daily prepared).
3. Add equal volume of NaOH-citrate-NALC into each clinical sample.
4. Vortex for 30 second and invert sample tube for several times keep in room temperature (RT) for 15 minutes.
5. Add PBS to 50 ml level of sample tube, then centrifuge at 3000 rpm for 20 minutes.

6. Remove supernatant and use 1 ml of PBS to resuspend precipitate.

II. Lysis of Precipitate (can be Performed in P2 Laboratory)
1. Mix 10 ml ddH$_2$O with 1 ml of resuspended precipitate. Vortex 20 sec, then centrifuge at 3,800 rpm for 15 min.
2. Remove supernatant; add 150 µl of Lysis buffer I and vortex for 1 min. Keep at RT for 10 min.
3. Keep Lysis tube in 100° C. water bath for 20 min and then add 125 µl of Lysis buffer II.
4. Centrifuge at 10,000 rpm for 2 min, collect DNA lysate and store it in −20° C. freezer.

III. Target Amplification:
1. Set up a new 0.2 ml microfuge tube by adding up the following reagent:

| Reagent | Volume |
| --- | --- |
| DNA | 1 µl |
| Reaction mixture * | 49 µl |

* The reaction mixture contains the following cocktail:

| Reagent | Volume |
| --- | --- |
| 10X extension buffer | 5 µl |
| #1 primer (GCACGTCGCGGACCTCC) | 5 µl |
| #2 primer (CGCCGCGATCAAGGAG) | 5 µl |
| dNTP | 1 µl |
| Taq DNA polymerase (2U/µl) | 0.5 µl |
| ddH$_2$O | 32.5 µl |

2. Initiate the following program with heated lid enabled

Extension Program:

| | Temperature | Time | Number of cycles |
| --- | --- | --- | --- |
| 1 | 94° C. | 3 min | 1 cycle |
| 2 | 94° C. | 1 min | 40 cycles |
| | 55° C. | 1 min | |
| | 72° C. | 30 sec | |
| 3 | 72° C. | 5 min | 1 cycle |
| 4 | 4° C. | Hold | — |

IV. Hybridization
1. In a hybridization tube, mix 115 µl of ddH$_2$O, 15 µl of MagProbe, 150 µl of hybridization buffer and 20 µl of each amplified DNA sample together.
2. Keep hybridization tubes at 95° C. dry bath for 5 min.
3. Transfer hybridization tubes to a 60° C. dry bath and hold for 20 min.
4. Transfer hybridization tubes to magnetic wells of a magnetic dry bath and hold for 5 min.
5. Remove hybridization buffer by aspiration.
6. Add 1 ml of pre-heated 60° C. Wash buffer to each tube, vortex and put tubes back to magnetic wells and hold for 5 min.
7. Remove hybridization buffer by aspiration.
8. Repeat Step 6-7.
9. Keep hybridization tubes at RT.

V. Detection
1. Add 200 µl of blocking solution into each tube, vortex.
2. Add 5 µl of freshly prepared BC (99 µl 0.1% PBST+1 µBC stock), vortex and disperse evenly. Sit at RT for 20 min. Avoid light.
3. Put hybridization tubes into magnetic rack and sit for 5 min. Then remove solution by aspiration.
4. Add 1 ml of 0.5% PBST, vortex and put tubes back to magnetic rack. Sit for 5 min then remove solution by aspiration. Repeat once.
5. Use 200 µl of PBS each tube to resuspend magnetic beads by vortexing.
6. Take 20 µl of resuspend solution from step 5.
7. Add 50 µl of mixed substrate to each tube (25 µl substrate A+25 µl substrate B).
8. Read luminescence by Luminometer.

VI. Interpretation of Results (the same Interpretation)
1. ≧100,000 RLU: Positive for drug-sensitive *M. tuberculosis*
2. <25,000 RLU: Positive for drug-resistant *M. tuberculosis*
3. 25,000~100,000 RLU: Probable drug-resistant *M. tuberculosis* positive;

Retest to verify results.
1. Retest value≧25,000 RLU: Positive for drug-sensitive *M. tuberculosis*.
2. Retest value<25,000 RLU: Positive for drug-resistant *M. tuberculosis*

Example 2

Following the above procedures, ten fentogram (10 fg) of genomic DNA from wild type *M. tuberculosis* were analyzed using five probes: P1, P2, P3, P4 and P5. It is clearly indicated in FIG. 2 that the probe 1, 2 and 5 showed high RLU value when reacting with genomic DNA from wild type *M. tuberculosis* strains W191 and W192.

Example 3

As indicated in FIG. 3, probe P1, P2, P3, P4 and P5 exhibited high RLU value when reacted with wild type *M. tuberculosis* strains W191 and W192 but low RLU when reacted with Rifampin-resistant *M. tuberculosis* strains Y94, P80 and Y194.

Example 4

Figure 4:
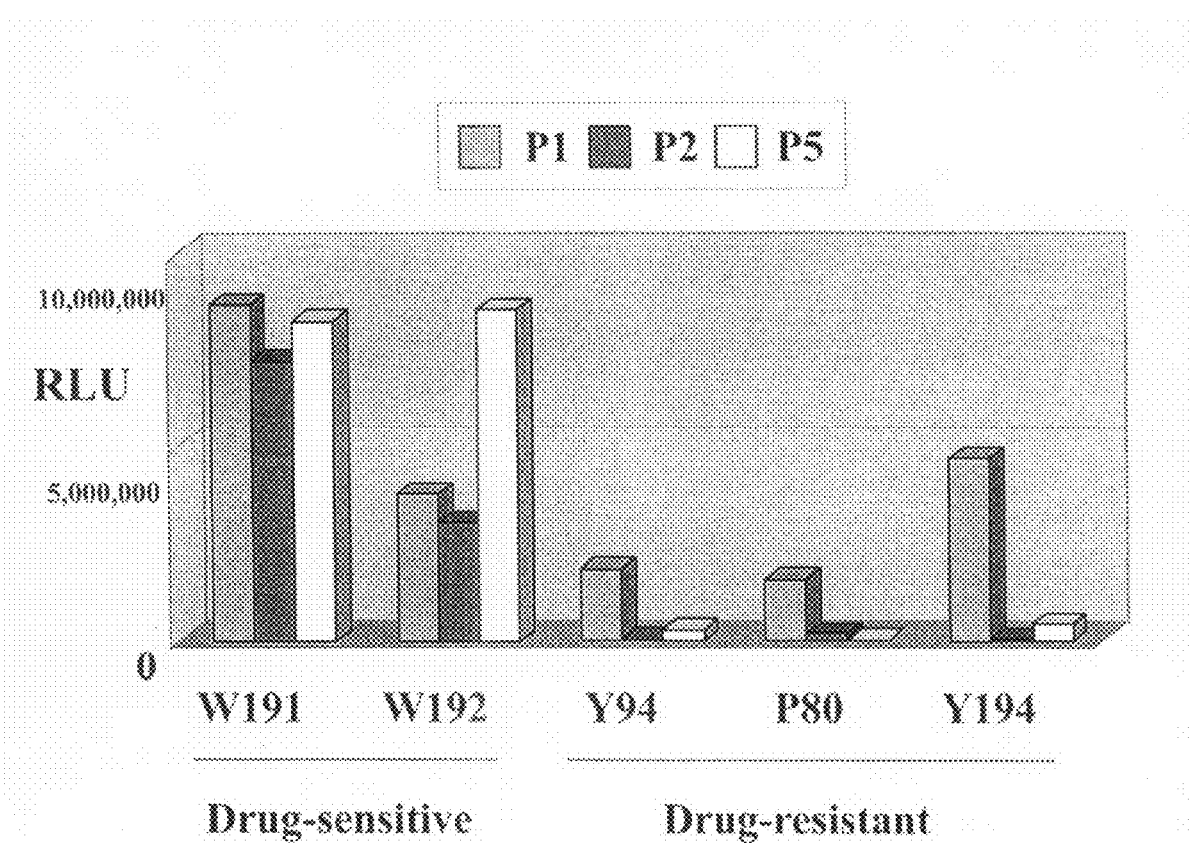
FIG. 4 shows the differentiation of drug-sensitive *M. tuberculosis* strains W191 and W 192 from drug-resistant *Mycobacterium tuberculosis* Y94, P80 and Y194 using probe P1, P2 and P5.

Different samples were assayed by the assay system of the invention. As indicated in FIG. 4, probe P1, P2 and P5 clearly differentiates drug-sensitive *M. tuberculosis* strains W191 and W192 from Rifampin-resistant strains Y94, P80 and Y194.

Example 5

Figure 5:
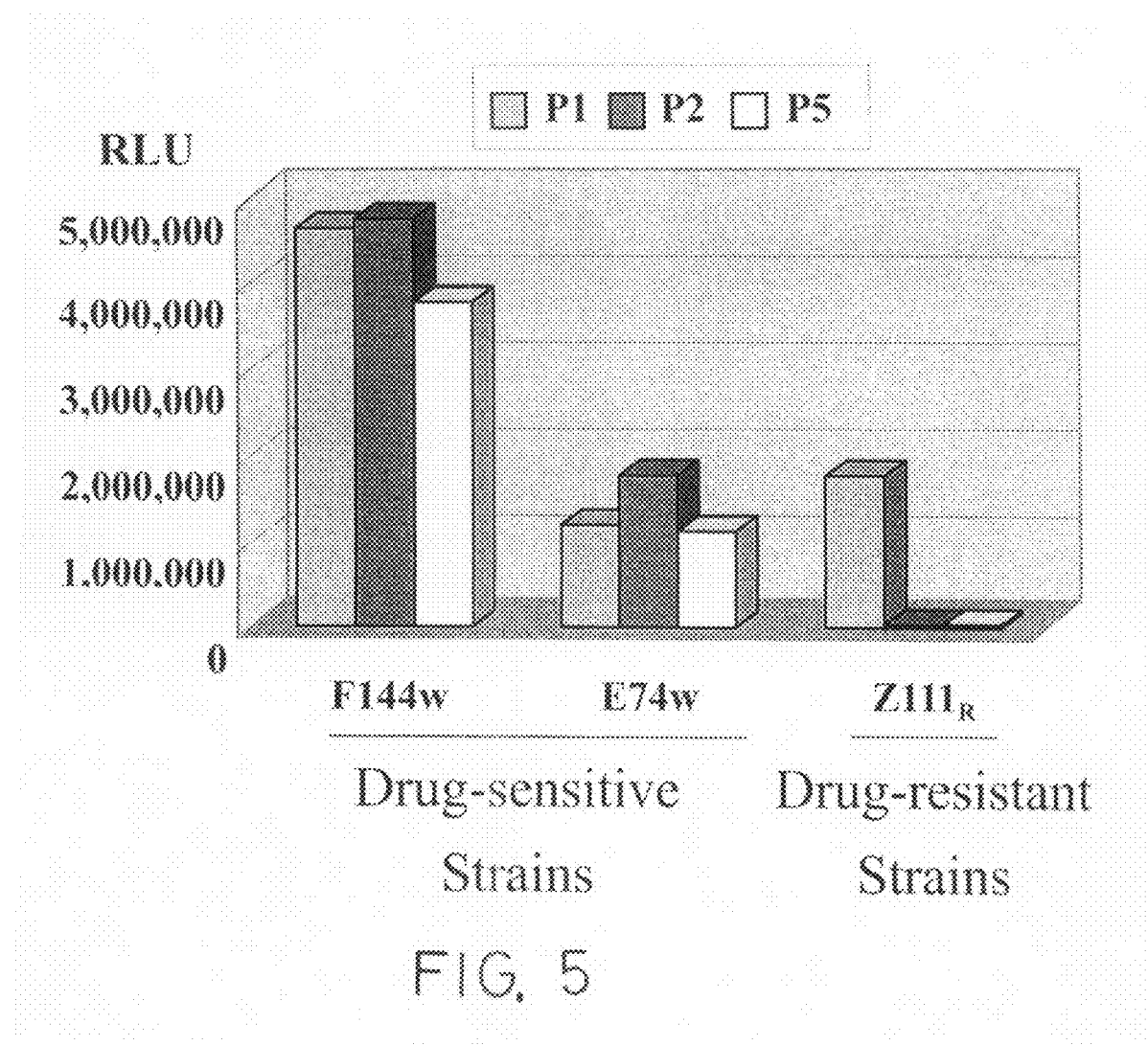
FIG. 5 shows the differentiation of drug-sensitive *Mycobacterium tuberculosis* strains F144w and E74w from drug-resistant *Mycobacterium tuberculosis* Z111R using probe P1, P2 and P5

Different samples were assayed by the assay system of the invention. As indicated in FIG. 5, probe P1, P2 and P5 clearly differentiates drug-sensitive *M. tuberculosis* strains F144w and E74w from Rifampin-resistant strains Z111R. The results in FIG. 5 were identical to that mentioned prior. These results had shown that the drug-resistant *M. tuberculosis* detection kits of the invention achieved extremely high sensitivity and specificity.

While the invention has been described and exemplified in sufficient detail for those skilled in this art to produce and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cell lines, embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed is:

1. A diagnostic kit for detecting drug-resistant *Mycobacterium tuberculosis* cDNA comprising:
- (a) probes P1, P2 and P5 wherein each probe is linked to a separate magnetic bead;
- (b) bioactive primers with DNA labeling reagents wherein the DNA reagents are the compounds having the formula;

Fu-BE-D wherein Fu represents a furocoumarin selected from the group consisting of angelicin and psoralen; BE represents none or a binding enhancer selected from the group consisting of C4-12 alkyl, alkyenyl, polyalkylamine and polyethylene glycol; and D represents a detectable group selected from the group consisting of: biotin, fluorescence, acridinium ester and acridinium-9-carboxamide, provided that D is biotin;
- (c) avidin enzyme complex or streptavidin enzyme complex; and
- (d) enzyme substrate, wherein the probe P1 is selected from the group consisting of:

| | |
|---|---|
| 5'-CAGCCAGCTGAGCCAATTCAT-3', | (SEQ ID NO:1) |
| 5'-CAGCCAGCTGAGCCAATTCATGGAC-3', | (SEQ ID NO:2) |
| 5'-CAGCCAGCTGAGCCAATTCATGGA-3', | (SEQ ID NO:3) |
| 5'-CAGCCAGCTGAGCCAATTCATGG-3', | (SEQ ID NO:4) |
| 5'-CAGCCAGCTGAGCCAATTCATG-3', | (SEQ ID NO:5) |
| 5'-CAGCCAGCTGAGCCAATTC-3', | (SEQ ID NO:6) |
| 5'-CAGCCAGCTGAGCCAATTCA-3', | (SEQ ID NO:7) |
| 5'-AGCCAGCTGAGCCAATTCATGG-3', | (SEQ ID NO:8) |
| 5'-GCCAGCTGAGCCAATTCATGGA-3', and | (SEQ ID NO:9) |
| 5'-GCCAGCTGAGCCAATTCCATG-3'; | (SEQ ID NO:10) | wherein the probe P2 is selected from the group consisting of:

| | |
|---|---|
| 5'-TTCATGGACCAGAACAACCCGCT -3', | (SEQ ID NO:11) |
| 5'-TTCATGGACCAGAACAACCCGC -3', | (SEQ ID NO:12) |
| 5'-TTCATGGACCAGAACAACCCG -3', | (SEQ ID NO:13) |
| 5'-TTCATGGACCAGAACAACCC -3', | (SEQ ID NO:14) |
| 5'-TTCATGGACCAGAACAACC -3', | (SEQ ID NO:15) |
| 5'-ATTCATGGACCAGAACAACCCGC -3', | (SEQ ID NO:16) |
| 5'-AATTCATGGACCAGAACAACCCG -3', | (SEQ ID NO:17) |
| 5'-CAATTCATGGACCAGAACAACCC -3', | (SEQ ID NO:18) |
| 5'-CCAATTCATGGACCAGAACAACC -3', | (SEQ ID NO:19) |
| 5'-CAATTCATGGACCAGAACAAC -3', and | (SEQ ID NO:20) |
| 5'-AATTCATGGACCAGAACAACCCGCT -3'; and | (SEQ ID NO:21) | wherein the probe P5 is selected from the group consisting of:

| | |
|---|---|
| 5'-CGACTGTCGGCGCTGGGGC-3', | (SEQ ID NO:22) |
| 5'-CGACTGTCGGCGCTGGGGCC-3', | (SEQ ID NO:23) |
| 5'-CGACTGTCGGCGCTGGGGCCC-3', | (SEQ ID NO:24) |
| 5'-CGACTGTCGGCGCTGGGGCCCG-3', | (SEQ ID NO:25) |
| 5'-CGACTGTCGGCGCTGGGGCCCGG-3', | (SEQ ID NO:26) |
| 5'-CGACTGTCGGCGCTGGGGCCCGGC-3', | (SEQ ID NO:27) |
| 5'-CCGACTGTCGGCGCTGGGGC-3', | (SEQ ID NO:28) |
| 5'-GCCGACTGTCGGCGCTGGGGC-3', | (SEQ ID NO:29) |
| 5'-CGCCGACTGTCGGCGCTGGGGC-3', | (SEQ ID NO:30) |
| 5'-GCGCCGACTGTCGGCGCTGGGGC-3', | (SEQ ID NO:31) |
| 5'-AGCGCCGACTGTCGGCGCTGGGGC-3', | (SEQ ID NO:32) |
| 5'-GACTGTCGGCGCTGGGGCC-3', | (SEQ ID NO:33) |
| 5'-ACTGTCGGCGCTGGGGCCC-3', | (SEQ ID NO:34) |
| 5'-CTGTCGGCGCTGGGGCCCG-3', | (SEQ ID NO:35) |
| 5'-CCGACTGTCGGCGCTGGGG-3', | (SEQ ID NO:36) |
| 5'-GCCGACTGTCGGCGCTGGG-3', and | (SEQ ID NO:37) |
| 5'-CGCCGACTGTCGGCGCTGGG-3'; and | (SEQ ID NO:38) | wherein positive detection of drug-resistant *Mycobacterium tuberculosis* cDNA is indicated when (i) the luminescence or color change associated with P1 is greater than the luminescence or color change associated with both P2 and P5, (ii) the luminescence or color change associated with P2 is less than the luminescence or color change associated with a P2 control, and (iii) the luminescence or color change associated with the P5 is less than the luminescence or color change associated with a P5 control, wherein control cDNA is drug-sensitive *Mycobacterium tuberculosis* cDNA.

2. The kit of claim 1, wherein the DNA labeling reagent is 9-(4"-(Aminomethyl)-4',5"-Dimethyl-angelicin)acridinium carboxamide.

* * * * *